US009020159B2

(12) United States Patent
Mori et al.

(10) Patent No.: US 9,020,159 B2
(45) Date of Patent: Apr. 28, 2015

(54) NOISE REDUCTION DEVICE

(75) Inventors: Keiji Mori, Osaka (JP); Hiroyuki Kano, Hyogo (JP); Tsuyoshi Maeda, Hyogo (JP); Yoshifumi Asao, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 708 days.

(21) Appl. No.: 12/641,732

(22) Filed: Dec. 18, 2009

(65) Prior Publication Data

US 2010/0166202 A1 Jul. 1, 2010

(30) Foreign Application Priority Data

Dec. 26, 2008 (JP) ................................ 2008-332544

(51) Int. Cl.
*A61F 11/06* (2006.01)
*G10K 11/178* (2006.01)

(52) U.S. Cl.
CPC .... *G10K 11/1786* (2013.01); *G10K 2210/1281* (2013.01); *G10K 2210/3055* (2013.01); *G10K 2210/3027* (2013.01); *G10K 2210/3221* (2013.01)

(58) Field of Classification Search
CPC ................. G10K 11/1786; G10K 2210/1281; G10K 2210/3027; G10K 2210/3055; G10K 11/1788; G10K 2210/1291; G10K 2210/129; G10K 2210/501; G10K 2210/30232; G10K 11/178
USPC .......... 381/71.11, 71.8, 71.1, 71.2, 71.4, 150, 381/122
See application file for complete search history.

(56) References Cited

U.S. PATENT DOCUMENTS

| | | | | |
|---|---|---|---|---|
| 5,170,433 | A | 12/1992 | Elliott et al. | |
| 5,426,703 | A | 6/1995 | Hamabe et al. | |
| 5,687,075 | A * | 11/1997 | Stothers | 700/28 |
| 5,689,572 | A | 11/1997 | Ohki et al. | |
| 5,701,350 | A * | 12/1997 | Popovich | 381/71.11 |
| 6,330,336 | B1 | 12/2001 | Kasama | |
| 7,343,016 | B2 * | 3/2008 | Kim | 381/71.12 |
| 2003/0219131 | A1 | 11/2003 | Akiho | |
| 2005/0015252 | A1 * | 1/2005 | Marumoto | 704/234 |

(Continued)

FOREIGN PATENT DOCUMENTS

| | | | |
|---|---|---|---|
| JP | 02-285799 | A | 11/1990 |
| WO | 01/63594 | A2 | 8/2001 |

(Continued)

OTHER PUBLICATIONS

Fuccio, M.L. et al "The DSP32C: AT&T's Second-Generation Floating-Point Digital Signal Processor", Dec. 1988, IEEE Micro, vol. 8, Issue 6. pp. 30-48.*
The Extended European Search Report dated Nov. 6, 2014 for the related European Patent Application No. 09180769.3.

*Primary Examiner* — Vivian Chin
*Assistant Examiner* — Con P Tran
(74) *Attorney, Agent, or Firm* — Pearne & Gordon LLP

(57) ABSTRACT

A noise control device includes the following structural elements. A signal memory records both of a noise signal supplied from a noise microphone and an error signal supplied from an error microphone. A filter coefficient calculator calculates a fixed filter coefficient of a control filter by using data recorded in the signal memory. A filter coefficient renewing section renews, at a given timing, a filter coefficient set at a fixed filter in a control filter to a filter coefficient read out from the filter coefficient calculator.

5 Claims, 15 Drawing Sheets

(56) References Cited

U.S. PATENT DOCUMENTS

| | | | | |
|---|---|---|---|---|
| 2007/0076896 | A1* | 4/2007 | Hosaka et al. | 381/71.11 |
| 2008/0159553 | A1* | 7/2008 | Copley et al. | 381/71.1 |
| 2010/0027804 | A1 | 2/2010 | Kano | |

FOREIGN PATENT DOCUMENTS

| | | | |
|---|---|---|---|
| WO | 2004/056298 | A1 | 7/2004 |
| WO | 2009/084186 | A1 | 7/2009 |

* cited by examiner

Seat : I
Time : t1~t2
Filter coefficient : coefficient (1)

Seat : I
Time : t3~t4
Filter coefficient : coefficient (2)

Seat : II
Time : t5~t6
Filter coefficient : coefficient (3)

Seat : I
Time : t3~t4
Filter coefficient : coefficient (1)

Seat : I
Time : t1~t2
Filter coefficient : coefficient (2)

Seat : II
Time : t5~t6
Filter coefficient : coefficient (1)

NOISE REDUCTION DEVICE

FIELD OF INVENTION

The present invention relates to a noise control device, and more particularly, it relates to a noise control device that can actively reduce the noises arriving at a control point.

BACKGROUND OF INVENTION

In an aircraft or a coach where passengers are always involved with noises, the passengers at the seats sometimes cannot clearly catch information provided through audio, such as an in-flight notice, due to the noises around the seats.

The aircraft or the coach defines an interior space with continuous walls, so that the interior space forms a kind of hermetic structure. If noise sources exist inside and outside the interior space, the passengers in the interior space are to be confined within a regular noise environment. An excess noise sometimes invites physical or mental stress to the passengers, thereby degrading the comfortableness in the interior space. In the case of an aircraft, in particular, although flight attendants try to provide the passengers with good service in the interior space, the noise becomes a critical problem to a service quality.

In the case of the aircraft, the following noises are chiefly involved: noises produced by the devices such as a propeller or an engine which generates thrust force for the aircraft, and noises, such as zip sound, involved with airstream produced by the movement of the aircraft in the air. The foregoing noises audible in the interior space make the passengers unpleasant and also hinder the in-flight audio notice. The noises thus need to be reduced.

Passive attenuating measures have been taken, in general, for reducing the noises in the hermetic space. This method places sound insulating material, such as a diaphragm or sound absorption material, between the hermetic structure and the noise source. The diaphragm includes, e.g. a high density diaphragm, and the sound absorption material includes, e.g. an acoustical sheet, which is, however, a high density member and thus becomes a weight gaining coefficient. An increment in the weight consumes a greater amount of fuel or reduces a flight range. As a result, the increment in the weight incurs degrading the economical performance of the aircraft. On top of that, the foregoing materials have a problem of strength such as being subject to damages and a problem of design such as having a poor quality image.

To overcome the disadvantages of the foregoing passive attenuating measures, a noise control device has been recently proposed. This noise control device reproduces a control sound having a reverse phase to that of a noise arriving at a control point, thereby reducing the noise (an active noise control disclosed in e.g. Patent Literature 1). This control method is achieved by operating a fixed filter and an adaptive filter selectively.

The conventional noise control device discussed above is detailed hereinafter with reference to FIG. 15, which shows a circuit diagram of the conventional noise control device. In FIG. 15, the noise control device includes noise microphone 9101, adaptive filter 9201, control speaker 9401, error microphone 9501, and fixed filter 9601.

The noise control device shown in FIG. 15 selects adaptive filter 9201 for performing a noise control when noises are varied due to a position change of a noise source or a change in a noise production state, e.g. a change in a driving condition or an rpm of a fan. Noise microphone 9101 detects coming-noises supplied from a noise source, and then outputs a noise signal to adaptive filter 9201. Filter 9201 processes the noise signal by using a filter coefficient, thereby generating a control signal, which is then radiated as a control sound from speaker 9401 to a control point. Error microphone 9501 is placed at the control point for detecting the noise supplied from the noise source and arriving at the control point as well as the control sound supplied from control speaker 9401 and arriving at the control point. At error microphone 9501, the noise arriving at the control point interferes with the control sound supplied from control speaker 9401, and the difference between these noise and sound is detected as an error signal. Adaptive filter 9201 renews its own coefficient such that the error signal can be minimized. The renewal is done, e.g. by a Filtered-X_LMS method, which is referred to as a coefficient renewal process hereinafter. Adaptive filter 9201 thus can renew its own filter coefficient such that an optimum control signal can be generated in response to the noise having undergone the following change and arriving at the control point when the noise is changed due to the position change of the noise source or a change in the noise producing condition.

When the renewed filter coefficients converge on one coefficient, the noise control device shown in FIG. 15 selects fixed filter 9601, at which the converged filter coefficient is fixedly set, thereby controlling the noise. The noise control device shown in FIG. 15 thus operates the fixed filter or the adaptive filter selectively for carrying out the active noise control.

For instance, the noise typically representing the engine noise in an aircraft has an almost constant noise level, so that the filter coefficient scarcely needs to be renewed. However, if a passenger beats around the error microphone so that a noise of different level can occur momentarily, then adaptive filter 9201 renews the coefficient such that the noise can be cancelled instantaneously. This mechanism thus allows the control sound to adversely affect, so that it is afraid that the noise level can be higher than a noise level where the control sound is not yet reproduced, i.e. a level before the noise is controlled.

The noise control device shown in FIG. 15 selects adaptive filter 9201 for controlling the noise, so that it needs a circuit which can perform the coefficient renewal. As a result, the circuit cannot be downsized. On top of that, the renewal of the coefficient of adaptive filter 9201 needs to calculate the coefficient on a real time basis, so that a strict processing capability is required. What is worse, if a wrong filter coefficient is used, a wrong control sound is reproduced immediately, and the noise level becomes higher than that when the control sound is not reproduced, i.e. before the noise is controlled, and resultantly makes the passengers sometimes unpleasant.

LITERATURE OF RELATED ART

Patent Literature 1: Unexamined Japanese Patent Application Publication No. 1102-285799

SUMMARY OF INVENTION

The present invention aims to provide a noise control device which radiates a control sound toward a control point for reducing a given noise arriving at the control point. The noise control device of the present invention comprises the following structural elements:

a controlling noise detector for detecting a given coming-noise and outputting a controlling noise signal;

a control filter for processing the controlling noise signal supplied from the controlling noise detector by using a fixed filter coefficient set in advance, and thereby outputting a control signal;

a control speaker for radiating a control sound based on the control signal supplied from the control filter, and thereby reducing a given noise arriving at the control point;

an error detector placed at the control point for detecting an error signal between the noise and the control sound that is supplied from the control speaker;

a signal memory for storing the controlling noise signal supplied from the controlling noise detector and an error signal detected by the error detector;

a filter coefficient calculator for calculating a filter coefficient by using the controlling noise signal and the error signal both stored in the signal memory; and a filter coefficient renewing section for renewing, at a given timing, the fixed filter coefficient set at the control filter to a filter coefficient calculated by the filter coefficient calculator.

The foregoing noise control device of the present invention operates the control filter at the fixed coefficient set in advance, and renews the coefficient only when the condition meets a given one. This given condition refers to the cases in which the environment greatly changes, e.g. in the case of an aircraft, a case in which an aircraft is put into service, a case in which the seats are replaced, a case in which this noise control device is replaced due to malfunction, or a case in which a state of the engine of the aircraft is changed. The given condition thus does not refer to a momentary difference in the noise level as the related art refers to.

DESCRIPTION OF PREFERRED EMBODIMENTS

Before the exemplary embodiments of the present invention are demonstrated, the basic concept of the present invention is described hereinafter.

Figure 1C:
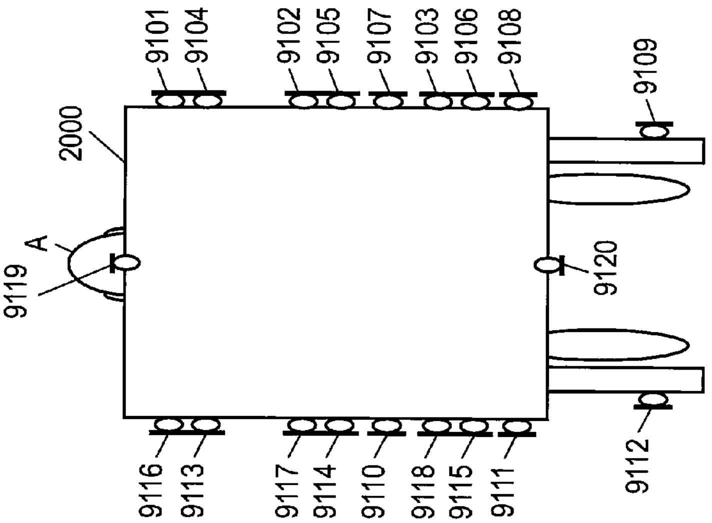
FIG. 1C shows a rear view illustrating the passenger seated in the aircraft.
Figure 1B:
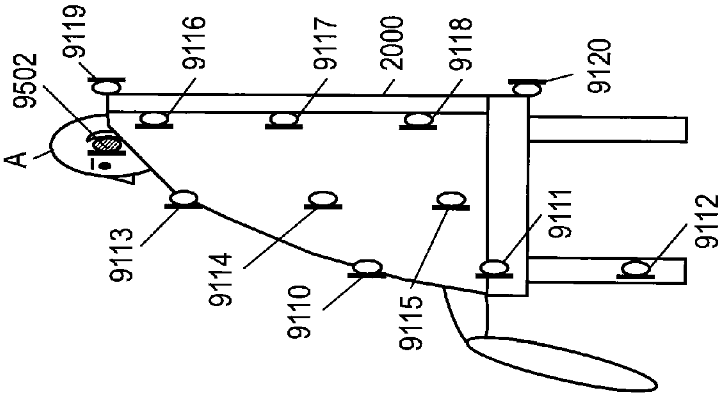
FIG. 1B shows a lateral view illustrating the passenger seated in the aircraft.
Figure 1A:
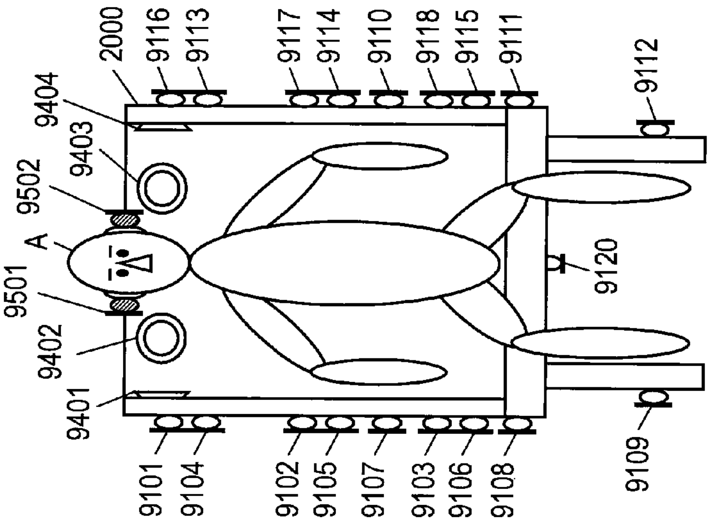
FIG. 1A shows a front view illustrating a passenger seated in an aircraft.
Figure 2:
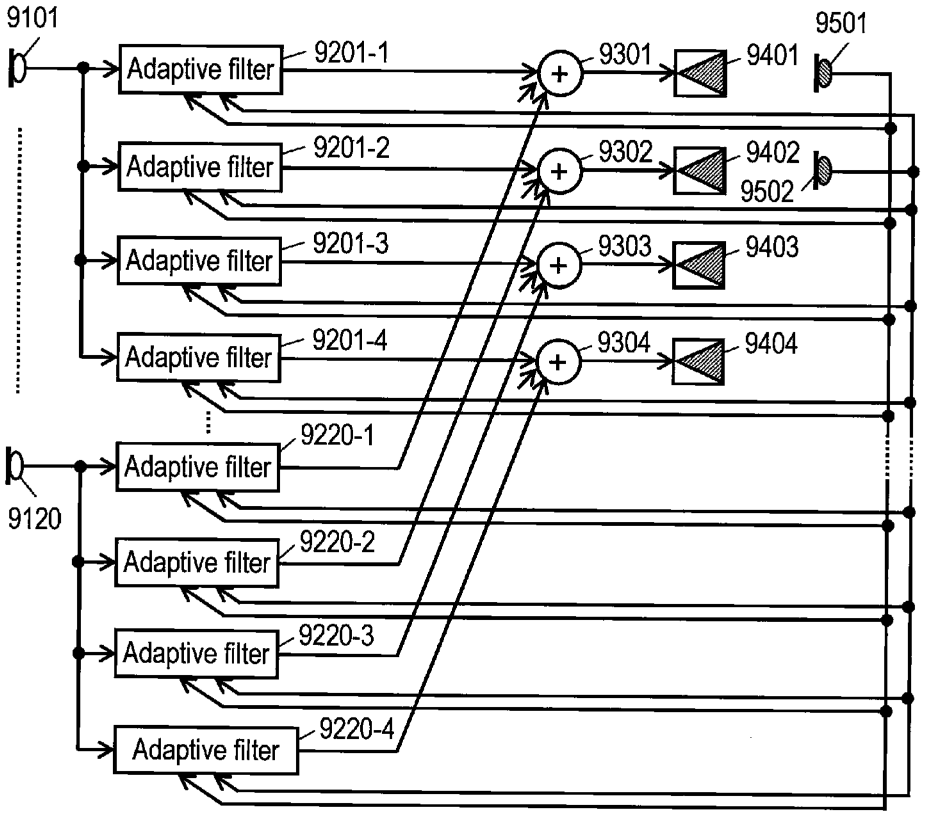
FIG. 2 shows a circuit diagram of a noise control device placed at a seat.

Assume that the noise control using an adaptive filter is carried out in an aircraft, and then the structure of the noise control will be shown in FIG. 1A-FIG. 1C and FIG. 2. FIG. 1A shows a front view of passenger A seated at seat 2000 in the aircraft. FIG. 1B shows a lateral view of passenger A, and FIG. 1C shows a rear view thereof. FIG. 2 shows a circuit diagram of the noise control device installed at seat 2000 shown in FIGS. 1A-1C.

As shown in FIG. 2, the noise control device includes the following structural elements:

noise microphones 9101-9120;
adaptive filters 9201-1-9220-1;
adaptive filters 9201-2-9220-2;
adaptive filters 9201-3-9220-3;
adaptive filters 9201-4-9220-4;
adders 9301-9304;
control speakers 9401-9404; and
error microphones 9501-9502.

As shown in FIG. 1, noise microphones 9101-9120 are placed outside seat 2000, and control speakers 9401-9404 are placed inside seat 2000 and close to the ears of passenger A in height. Control points are set at the ears of passenger A, and assume that error microphones 9501-9502 are placed close to the ears of passenger A, i.e. at the control points, although this placement is practically difficult.

A noise collected by noise microphone 9101 is supplied as a noise signal to adaptive filters 9201-1-9201-4. A noise collected by noise microphone 9102 is supplied as a noise signal to adaptive filters 9202-1-9202-4. In a similar way, noises collected by noise microphones 9103-9120 are supplied to corresponding adaptive filters 9203-1-9220-4 respectively.

Adaptive filter 9201-1 has a transfer function between control speaker 9401 and error microphone 9501 and a transfer function between control speaker 9401 and error microphone 9502. These transfer functions are necessary for the coming operation and have been set in filter 9201-1 in advance by the Filtered-X_LMS method. Using the transfer functions, adaptive filter 9201-1 renews its own filter coefficient such that the error signals supplied from error microphones 9501 and 9502 can be minimized in total.

Error microphones 9501-9502 are placed at the control points and collect the noise arriving at the control points and the control sound supplied from control speakers 9401-9404. The noise and the control sound interfere with each other at error microphones 9501-9502, and the differences between them are detected as error signals.

In a similar way, adaptive filter 9202-1 has a transfer function between control speaker 9401 and error microphone 9501 and a transfer function between control speaker 9401 and error microphone 9502. Using these transfer functions, adaptive filter 9202-1 renews its own filter coefficient such that the error signals supplied from error microphones 9501 and 9502 can be minimized in total.

Each one of adaptive filters 9203-1-9220-1 has a transfer function from control speaker 9401 to error microphone 9501 and a transfer function from control speaker 9401 to error microphone 9502. Using the transfer functions, each one of adaptive filters 9203-1-9220-1 renews its own filter coefficient such that the error signals supplied from error microphones 9501 and 9502 can be minimized in total.

Each one of adaptive filters 9201-2-9220-2 has a transfer function from control speaker 9402 to error microphone 9501 and a transfer function from control speaker 9402 to error microphone 9502. Using the transfer functions, each one of adaptive filters 9201-2-9220-2 renews its own filter coefficient such that the error signals supplied from error microphones 9501 and 9502 can be minimized in total.

Each one of adaptive filters 9201-3-9220-3 has a transfer function from control speaker 9403 to error microphone 9501 and a transfer function from control speaker 9403 to error microphone 9502. Using the transfer functions, each one of adaptive filters 9201-3-9220-3 renews its own filter coefficient such that the error signals supplied from error microphones 9501 and 9502 can be minimized in total.

Each one of adaptive filters 9201-4-9220-4 has a transfer function from control speaker 9404 to error microphone 9501 and a transfer function from control speaker 9404 to error microphone 9502. Using the transfer functions, each one of adaptive filters 9201-4-9220-4 renews its own filter coefficient such that the error signals supplied from error microphones 9501 and 9502 can be minimized in total.

Each one of adaptive filters 9201-1-9220-1 processes the supplied noise signal by using the renewed filter coefficient, and supplies the resultant signal as a control signal to adder 9301, which then adds the control signals together and supplies it to control speaker 9401. Control speaker 9401 radiates a control sound based on the control signal supplied from adder 9301 toward error microphones 9501 and 9502, i.e. the control points.

Each one of adaptive filters 9201-2-9220-2 processes the supplied noise signal by using the renewed filter coefficient, and supplies the resultant signal as a control signal to adder 9302, which then adds the control signals together and supplies it to control speaker 9402. Control speaker 9402 radiates a control sound based on the control signal supplied from adder 9302 toward error microphones 9501 and 9502, i.e. the control points.

Each one of adaptive filters 9201-3-9220-3 processes the supplied noise signal by using the renewed filter coefficient, and supplies the resultant signal as a control signal to adder 9303, which then adds the control signals together and supplies it to control speaker 9403. Control speaker 9403 radiates a control sound based on the control signal supplied from adder 9303 toward error microphones 9501 and 9502, i.e. the control points.

Each one of adaptive filters 9201-4-9220-4 processes the supplied noise signal by using the renewed filter coefficient, and supplies the resultant signal as a control signal to adder 9304, which then adds the control signals together and supplies it to control speaker 9404. Control speaker 9404 radiates a control sound based on the control signal supplied from adder 9304 toward error microphones 9501 and 9502, i.e. the control points.

The coefficient renewal processes discussed above allow the noise control device shown in FIG. 1 and FIG. 2 to reduce the noise arriving at the control points, i.e. the ears of passenger A.

Figure 3:
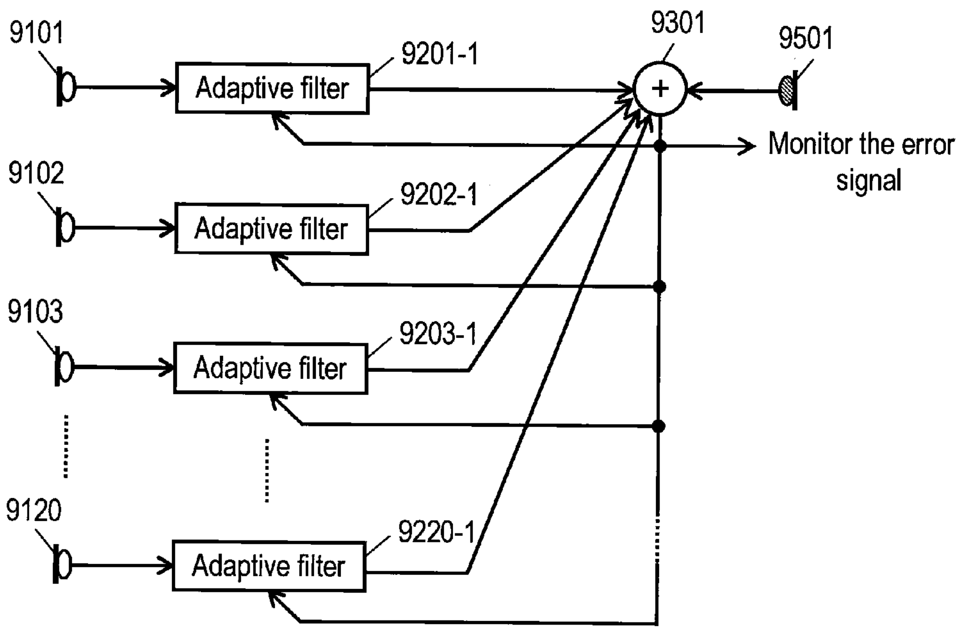
FIG. 3 shows a circuit diagram of a verification circuit.

In a case where the frequency of the noise and/or the noise level scarcely change, or they fluctuate within a certain range, a noise control using only fixed filters can achieve almost the same noise reduction effect as the noise control using the adaptive filters. This can be proved by the following demonstration:

A verification circuit shown in FIG. 3 is placed at seat 2000, and error signals are monitored with the seat position and the time condition varied. The verification circuit shown in FIG. 3 is described specifically hereinafter. The noise signals supplied from noise microphones 9101-9120 undergo the signal process in corresponding adaptive filters 9201-1-9220-1, and then the resultant noise signals are added together by adder 9301. The noise collected by error microphone 9501 is supplied to adder 9301. An adding result by adder 9301 is considered as an error signal, and adaptive filters 9201-1-9220-1 renew their own filter coefficients such that the error signal can be minimized. As a result, the adding result by adder 9301 can be reduced, which means that the noise collected by error microphone 9501 can be reduced.

Adaptive filters 9201-1-9220-1 shown in FIG. 2 renew their own filter coefficients by the Filtered-X_LMS method; however, the same filters shown in FIG. 3 renew their own filter coefficients by a general LMS method.

Figure 4:
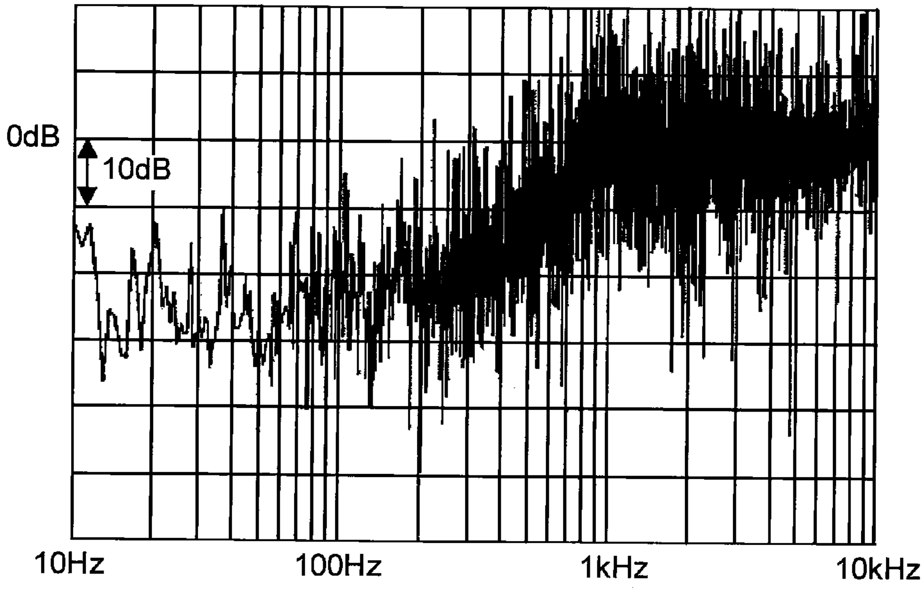
FIG. 4 shows a result of monitoring differences between error signals under the condition that a seat is placed at position I and the error signals are measured during times t1-t2.

The error signals are monitored with the seat position and the time condition varied when the filter coefficients of adaptive filters 9201-1-9220-1 converge on a certain value due to the coefficient renewal process discussed above. The error signals are monitored during a cruising of the aircraft, and the monitor results are described below:

FIG. 4 shows the monitoring result of the error signals under the condition that seat 2000 is placed at position I, and the error signal is monitored during times t1-t2. The result shows the difference between the error signal under control and the error signal under non-control. In other words, the error signal below 0 dB (zero decibel) means that the noise is reduced. Seat position I refers to as a window side and at a front section of the aircraft.

As shown in FIG. 4, the difference between the error signals lowers below ca. 1 kHz, and decreases by more than 10 dB below 500 Hz. A group of the converged filter coefficients of adaptive filters 9201-1-9220-1 used in this case is referred to as coefficient (1).

Figure 5:
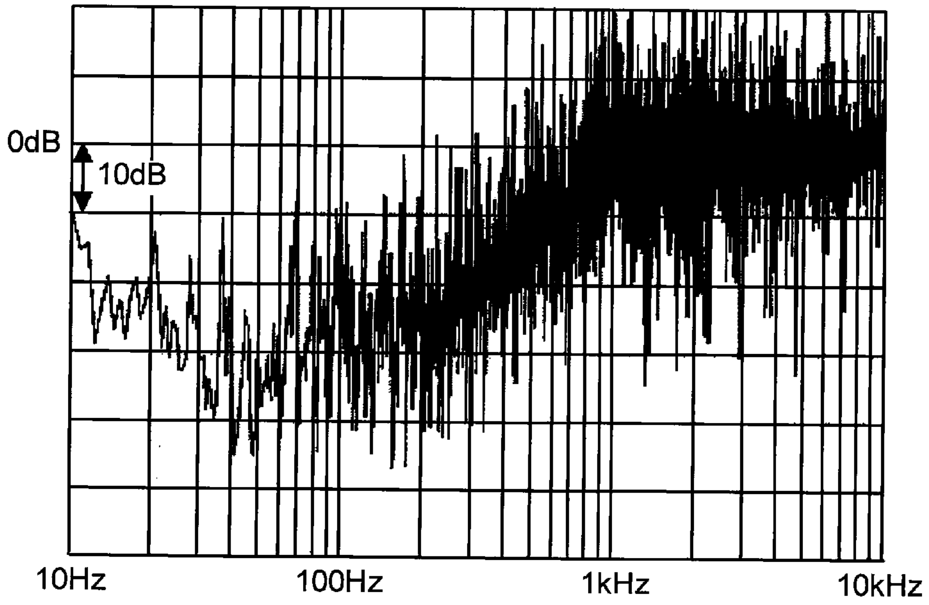
FIG. 5 shows a result of monitoring differences between error signals under the condition that the seat remains at position I and the error signals are measured during times t3-t4.

FIG. 5 shows the monitoring result of the error signals under the condition that seat 2000 remains at position I, and the error signal is monitored during times t3-t4. As shown in FIG. 5, the difference between the error signals lowers below ca. 1 kHz, and decreases by more than 10 dB below 500 Hz. This is a similar phenomenon to what is shown in FIG. 4. A group of the converged filter coefficients of adaptive filters 9201-1-9220-1 used in this case is referred to as coefficient (2).

Figure 6:
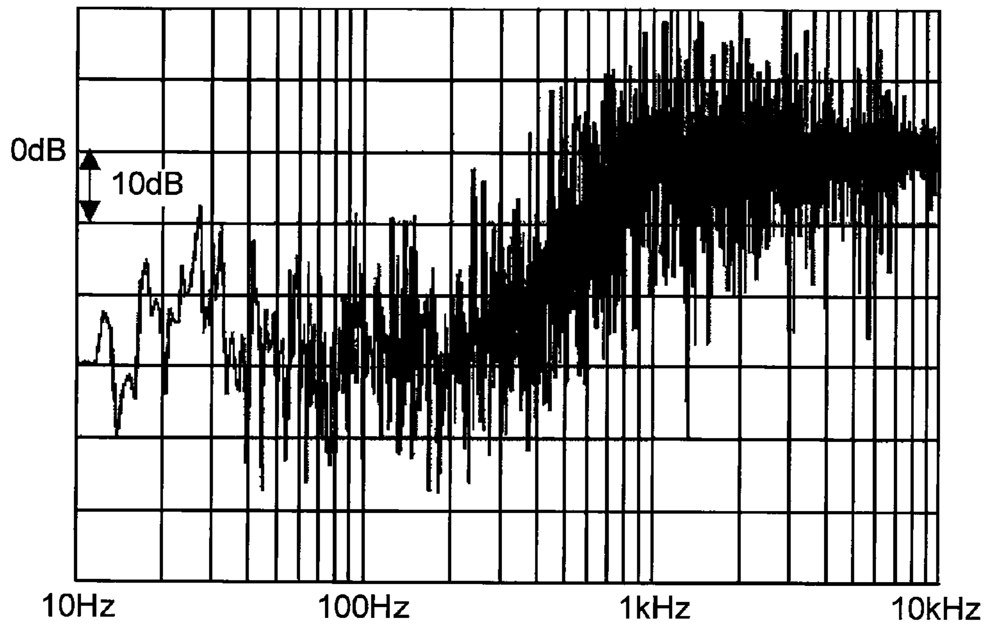
FIG. 6 shows a result of monitoring differences between error signals under the condition that a seat is placed at position II and the error signals are measured during times t5-t6.

FIG. 6 shows the monitoring result of the error signals under the condition that seat 2000 is placed at position II, and the error signal is monitored during times t5-t6. Seat position II is located at the center and at the front section of the aircraft. Since positions I and II are both located at the front section of the aircraft, they exist within a given area. As shown in FIG. 6, the difference between the error signals lowers below ca. 1 kHz, and decreases by more than 10 dB below 500 Hz. This is a similar phenomenon to what is shown in FIG. 4. A group of the converged filter coefficients of adaptive filters 9201-1-9220-1 used in this case is referred to as coefficient (3).

The time interval between times t2 and t3 as well as between times t4 and t5 is a sufficiently long span, e.g. over 30 minutes.

Figure 7:
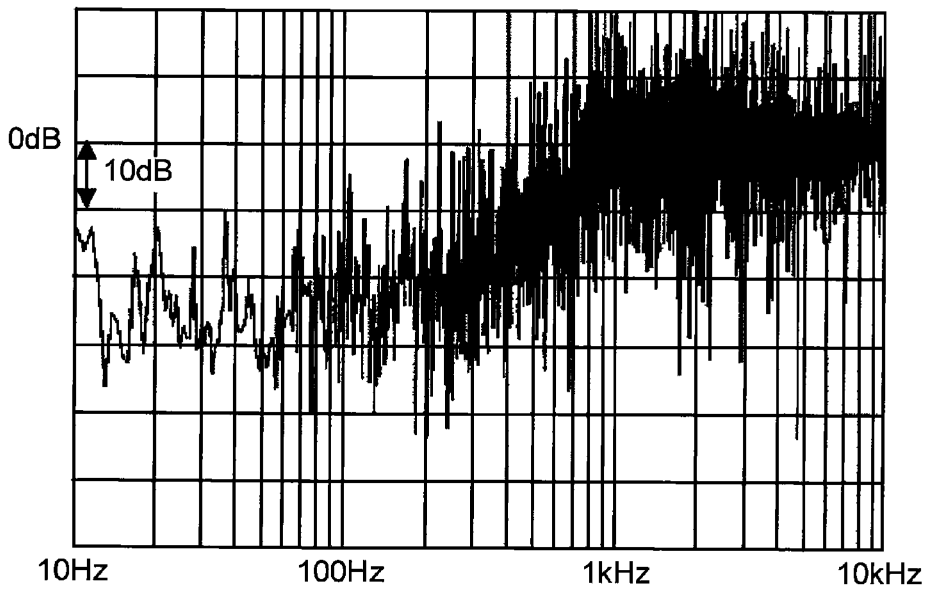
FIG. 7 shows a result of monitoring differences between error signals under the condition that a seat is placed at position I, the error signals are measured during times t3-t4, and a filter coefficient is fixed at (1).

The coefficient renewal process of adaptive filters 9201-1-9220-1 is halted under the condition of seat 2000 at position I and the error signal is measured during times t3-t4, then coefficient (1) is set to each one of the foregoing adaptive filters, which then work as fixed filters. In this condition, the difference between the error signals is monitored, and the result is shown in FIG. 7, which proves that the difference between the error signals exhibits a noise reduction effect, similar to that shown in FIG. 5, produced by controlling the noise with coefficient (2).

Figure 8:
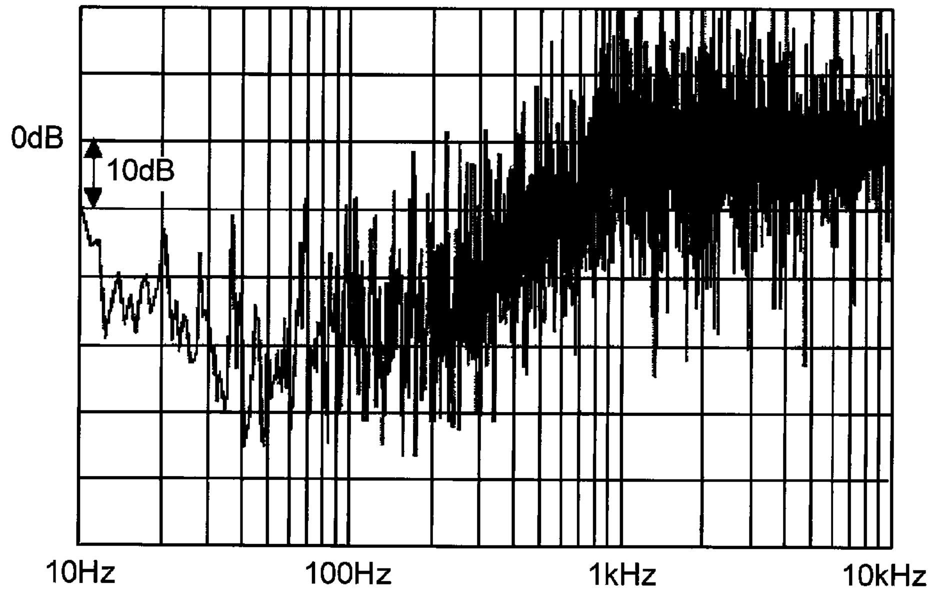
FIG. 8 shows a result of monitoring differences between error signals under the condition that a seat is placed at position I, the error signals are measured during times t1-t2, and a filter coefficient is fixed at (2).

To the contrary, the coefficient renewal process of adaptive filters 9201-1-9220-1 is halted under the condition of seat 2000 at position I and the error signal is measured during times t1-t2, then coefficient (2) is set fixedly to each one of the foregoing adaptive filters, which then work as fixed filters. In this condition, the difference between the error signals is monitored, and the result is shown in FIG. 8, which proves that the difference between the error signals exhibits a noise reduction effect, similar to that shown in FIG. 4, produced by controlling the noise with coefficient (1).

On top of that, the coefficient renewal process of adaptive filters 9201-1-9220-1 is halted under the condition of seat 2000 at position II and the error signal is measured between times t5-t6, then coefficient (1) is set fixedly to each one of the foregoing adaptive filters, which then work as fixed filters. In this condition, the difference between the error signals is monitored, and the result is shown in FIG. 9, which proves that the difference between the error signals exhibits a noise reduction effect, similar to that shown in FIG. 6, produced by controlling the noise with coefficient (3).

The monitoring discussed above reaches the following conclusion: The results shown in FIGS. 4, 7 and the results shown in FIGS. 5, 8 prove that when the noise is controlled with only the fixed filters in which filter coefficients found at different times are set fixedly, the passenger seated at least in the same seat obtains a noise reduction effect similar to a case where the noise is controlled only by the adaptive filters which always renew the filter coefficients.

In other words, even when the frequency of the noise and/or the noise level fluctuate within a certain range depending on time, the fixed filters can produce a noise reduction effect similar to the adaptive filters, which always renew the filter coefficients, can do.

Figure 9:
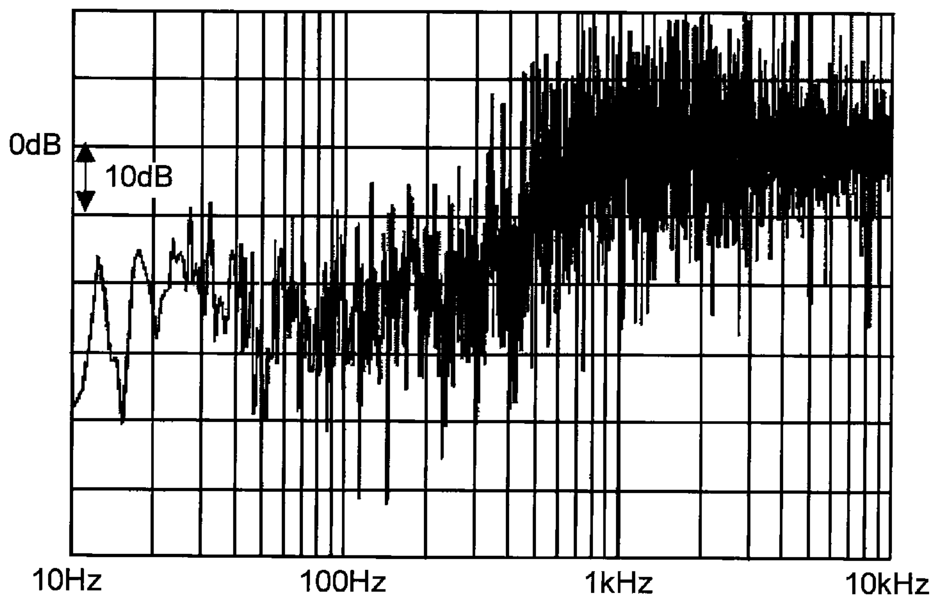
FIG. 9 shows a result of monitoring differences between error signals under the condition that a seat is placed at position II, the error signals are measured during times t5-t6, and a filter coefficient is fixed at (1).

The results shown in FIGS. 6 and 9 prove that the noise within a given area can be controlled only by the fixed filters, in which filter coefficients found at different places are set fixedly, thereby producing a noise reduction effect similar to a case where the noise is controlled only by the adaptive filters which always renew the coefficients.

In other words, even when the frequency of the noise and/or the noise level fluctuate within a certain range depending on place, the fixed filters can produce a noise reduction effect similar to the adaptive filters, which always renew the filter coefficients, can do.

As discussed above, in the case where the frequency of the noise and/or the noise level fluctuate within a certain range, such as in a given area of the cruising aircraft, the noise can be controlled only by the fixed filter in which filter coefficients found based on the noise are set fixedly, thereby producing a noise reduction effect similar to the effect produced through controlling the noise only by the adaptive filters.

However, in a case where the noise level seems steady, different seats sometimes receive different kinds of noise, so that fixed filters having optimum filter coefficients are not always prepared. Even if the filter coefficient prepared is optimum one to the initial stage, it is not necessarily kept as the optimum one for a long time because the seat position or the ambient environment can be changed due to a renewal or aging of in-flight equipment.

On top of that, in the case of using the fixed filters, the filter coefficient thereof must be found in some way. For instance, an aircraft have a large number of seats because it carries many people, so that each one of the seats needs its own optimum filter coefficient. Another model of aircraft has different body, engine, and seats. Even the same models employ different engines depending on airlines. It may thus require tremendous time and labor for fining the filter coefficients optimum to each one of these seats.

To solve the foregoing possible problem, the filter coefficient, set at the fixed filter in the case where the noise seems steady, is renewed to a coefficient optimum to a seat position and an ambient environment, thereby obtaining an optimum noise reduction effect in any time. At the same time, the renewal to the optimum filter coefficient can be done automatically, so that the time and labor necessary for fining the filter coefficient optimum to each seat can be greatly reduced.

Exemplary embodiments of the present invention are demonstrated hereinafter with reference to the accompanying drawings.

Embodiment 1

Figures 10A, 10B, 10C:
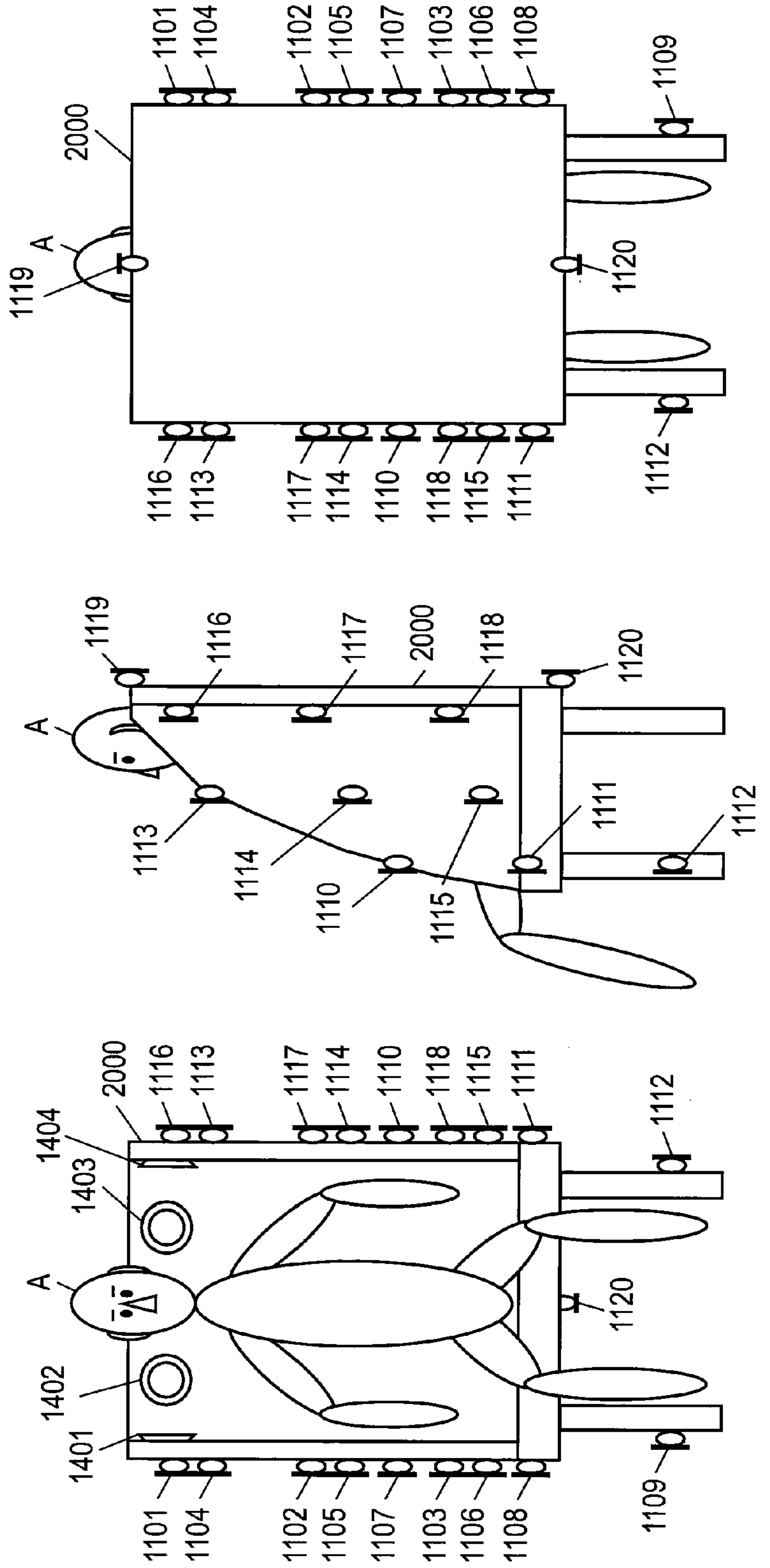
FIG. 10A shows a front view of a passenger seated in an aircraft.
FIG. 10B a lateral view illustrating the passenger seated in the aircraft.
FIG. 10C shows a rear view illustrating the passenger seated in the aircraft.
Figure 11:
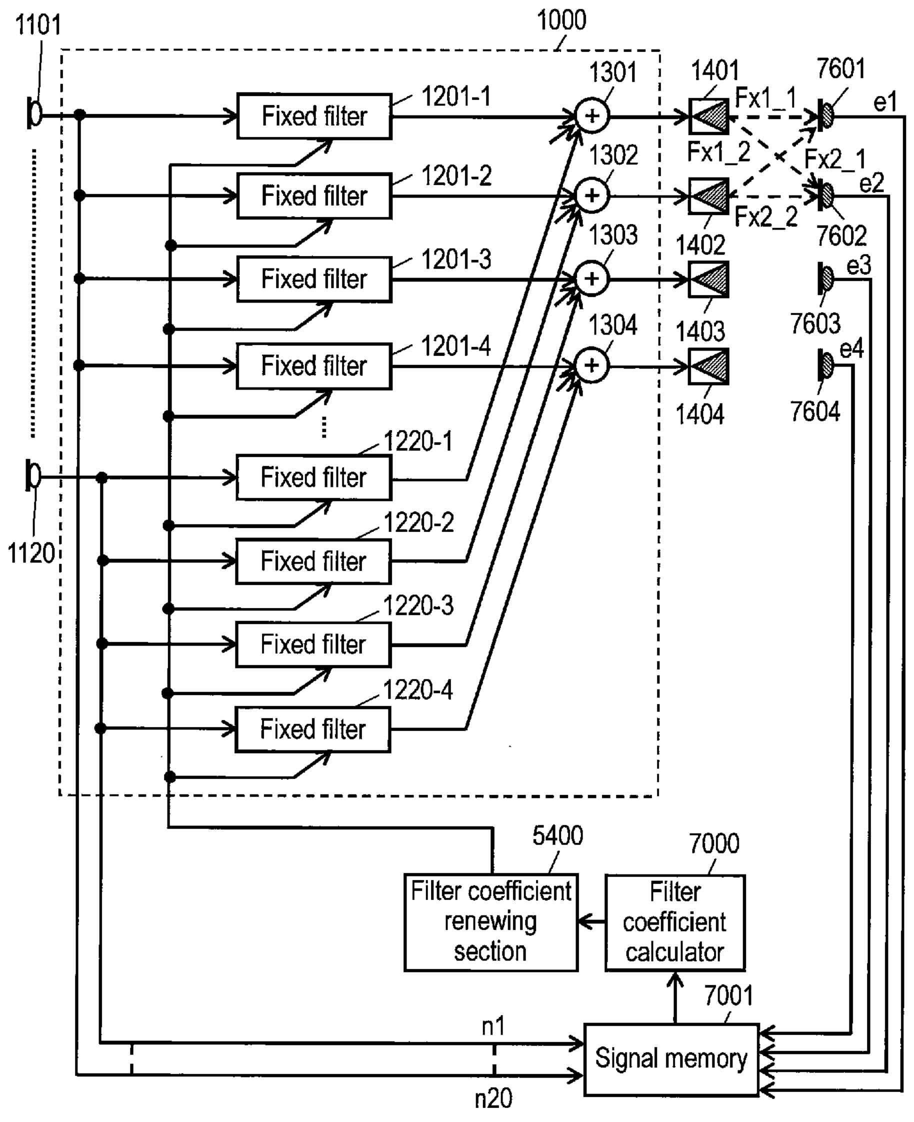
FIG. 11 shows a circuit diagram of a noise control device in accordance with a first embodiment of the present invention.

A circuit structure of the noise control device in accordance with the first embodiment is described hereinafter with reference to FIGS. 10A-10C and FIG. 11. FIG. 10A shows a front view of passenger A seated at seat 2000 of an aircraft. FIG. 10B shows a lateral view of passenger A, and FIG. 10C shows a rear view of passenger A. FIG. 11 shows the circuit diagram of the noise control device placed at seat 2000 shown in FIGS. 10A-10C and in accordance with the first embodiment.

As shown in FIG. 11, the noise control device comprises the following elements:

- noise microphones 1101-1120;
- control filter 1000;
- control speakers 1401-1404;
- filter coefficient renewing section 5400;
- filter coefficient calculator 7000;
- signal memory 7001; and
- error microphones 7601-7604.

As shown in FIG. 10, noise microphones 1101-1120 work as controlling noise detectors for detecting controlling noises. Placement of the noise microphones outside seat 2000 allows sensing the coming-noises and outputting them as controlling noise signals to control filter 1000. Control speakers 1401-1404 are placed inside seat 2000 at the same height as passenger A's ears, which are considered as the control points. Control speakers 1401-1404 receive the control signals produced by filter 1000, and then radiate controlling sounds toward the control points. Error microphones 7601-7604 are mounted to, e.g. the seat at the vicinity of passenger A's ears.

Operations of control filter 1000 and control speakers 1401-1404 are demonstrated hereinafter. Filter 1000 includes fixed filters 1201-1-1220-1, fixed filters 1201-2-1220-2, fixed filters 1201-3-1220-3, fixed filters 1201-4-1220-4, and adders 1301-1304.

A noise detected by noise microphone 1101 is supplied as a controlling noise signal to fixed filters 1201-1-1201-4. A noise detected by noise microphone 1102 is supplied as a controlling noise signal to 1202-1-1204-4. In a similar way, a noise detected by noise microphones 1103-1120 are supplied to corresponding fixed filters 1203-1-1220-4 respectively.

Fixed filter 1201-1 includes a filter coefficient, which has been set by filter coefficient calculator 7000 and filter coefficient renewing section 5400 both detailed later, and provides the controlling noise signal supplied from noise microphone 1101 with signal-process by using the filter coefficient, and then supplies the resultant signal as a control signal to adder 1301.

The filter coefficient to be set at filter 1201-1 is found this way: A control sound produced based on the control signal is supplied from control speaker 1401 and arrives at the control point where a given noise also arrives. The filter coefficient is found such that the phase of the control sound can be opposite to that of the given noise at the control point.

Assume that the given noise discussed above is a noise generated in the cruising aircraft, and the filter coefficients set at fixed filters 1201-1-1220-4 are found under the condition that the frequency of the noise arriving at the control point and/or the noise level fluctuate within a certain range.

Fixed filter 1202-1 includes a filter coefficient, which has been set by filter coefficient calculator 7000 and filter coefficient renewing section 5400 both detailed later, and provides the controlling noise signal supplied from microphone 1102 with signal-process by using the filter coefficient, and then supplies the resultant signal as a control signal to adder 1301.

The filter coefficient to be set at filter 1202-1 is found this way: A control sound produced based on the control signal is supplied from control speaker 1401 and arrives at the control point where a given noise also arrives. The filter coefficient is found such that the phase of the control sound can be opposite to that of the given noise at the control point.

In a similar way, fixed filters 1203-1-1220-1 include filter coefficients, which have been set by filter coefficient calculator 7000 and filter coefficient renewing section 5400 both detailed later, and provide the controlling noise signal supplied from corresponding microphone 1103-1120 with signal-process by using the filter coefficients, and then supply the resultant signals as control signals to adder 1301.

The filter coefficients to be set at filters 1203-1-1220-1 are found this way: A control sound produced based on the control signal is supplied from control speaker 1401 and arrives at the control point where a given noise also arrives. The filter coefficients are found such that the phase of the control sound can be opposite to that of the given noise at the control point.

Adder 1301 adds the control signals supplied from fixed filters 1201-1-1220-1 together, and then outputs the resultant signal to control speaker 1401, which then radiates the control sound based on the control signal supplied from adder 1301 toward the control point.

Fixed filter 1201-2-1220-2 include filter coefficients, which have been set by filter coefficient calculator 7000 and filter coefficient renewing section 5400 both detailed later, and provide the controlling noise signal supplied from corresponding microphone 1101-1120 with signal-process by using the filter coefficients, and then supply the resultant signals as control signals to adder 1302.

The filter coefficients to be set at filters 1201-2-1220-2 are found this way: A control sound produced based on the control signal is supplied from control speaker 1402 and arrives at the control point where a given noise also arrives. The filter coefficients are found such that the phase of the control sound can be opposite to that of the given noise at the control point.

Adder 1302 adds the control signals supplied from fixed filters 1201-2-1220-2 together, and then outputs the resultant signal to control speaker 1402, which then radiates the control sound based on the control signal supplied from adder 1302 toward the control point.

Fixed filter 1201-3-1220-3 include filter coefficients, which have been set by filter coefficient calculator 7000 and filter coefficient renewing section 5400 both detailed later, and provides the controlling noise signal supplied from corresponding microphone 1101-1120 with signal-process by using the filter coefficients, and then supply the resultant signals as control signals to adder 1303.

The filter coefficients to be set at filters 1201-3-1220-3 are found this way: A control sound produced based on the control signal is supplied from control speaker 1403 and arrives at the control point where a given noise also arrives. The filter coefficients are found such that the phase of the control sound can be opposite to that of the given noise at the control point.

Adder 1303 adds the control signals supplied from fixed filters 1201-3-1220-3 together, and then outputs the resultant signal to control speaker 1403, which then radiates the control sound based on the control signal supplied from adder 1303 toward the control point.

Fixed filter 1201-4-1220-4 include filter coefficients, which have been set by filter coefficient calculator 7000 and filter coefficient renewing section 5400 both detailed later, and provide the controlling noise signal supplied from corresponding microphone 1101-1120 with signal-process by using the filter coefficients, and then supply the resultant signals as control signals to adder 1304.

The filter coefficients to be set at filters 1201-4-1220-4 are found this way: A control sound produced based on the control signal is supplied from control speaker 1404 and arrives at the control point where a given noise also arrives. The filter coefficients are found such that the phase of the control sound can be opposite to that of the given noise at the control point.

Adder 1304 adds the control signals supplied from fixed filters 1201-4-1220-4 together, and then outputs the resultant signal to control speaker 1404, which then radiates the control sound based on the control signal supplied from adder 1304 toward the control point.

The foregoing processes done by control filter 1000 allow reducing the given noise arriving at passenger A's ears, i.e. the control points.

Next, operations of filter coefficient renewing section 5400, filter coefficient calculator 7000, signal memory 7001, and error microphones 7601-7604 are described hereinafter. Four error microphones are prepared in this first embodiment for sensing noises at their places; however, the number of speakers can be equal to or less than the number of the control speakers because this number of error microphones can find accurately the control coefficient of the fixed filters in theory.

Acoustic characteristic between control speaker 1401 and error microphone 7601 is indicated as Fx1_1, and that between speaker 1401 and error microphone 7602 is indicated as Fx1_2, and that between speaker 1402 and error microphone 7601 is indicated as Fx2_1, and that between speaker 1402 and microphone 7602 is indicated as Fx2_2. Other acoustic characteristics Fx1_3, Fx4_2 between speaker 1401 and microphone 7603, and between speaker 1404 and microphone 7602 are omitted in FIG. 12.

Error microphones 7601-7604 are placed at the control points for sensing noises supplied from noise sources and arriving at the control points as well as the control sounds supplied from control speakers 1401-1404 and arriving at the control points. At error microphones 7601-7604, the noises arriving at the control points interfere with the control sounds arriving at the control points, and the differences between the noises and the control sounds are detected as error signals.

Signal memory 7001 records noise signals n1-n20 supplied from noise microphones 1101-1120 as well as error signals e1-e4 supplied from error microphones 7601-7604 in an internal memory for a given time. When the recording ends, signal memory 7001 gives an instruction to filter coefficient calculator 7000 that calculator 7000 should start calculating a coefficient, then calculator 7000 calculates the filter coefficients for the fixed filters of control filter 1000 by using the data recorded in memory 7001.

Filter coefficient renewing section 5400 reads the filter coefficients calculated by calculator 7000 at a given timing, and renews the filter coefficients set at the fixed filters of control filter 1000 to the filter coefficients read-out from calculator 7000.

Figure 12:
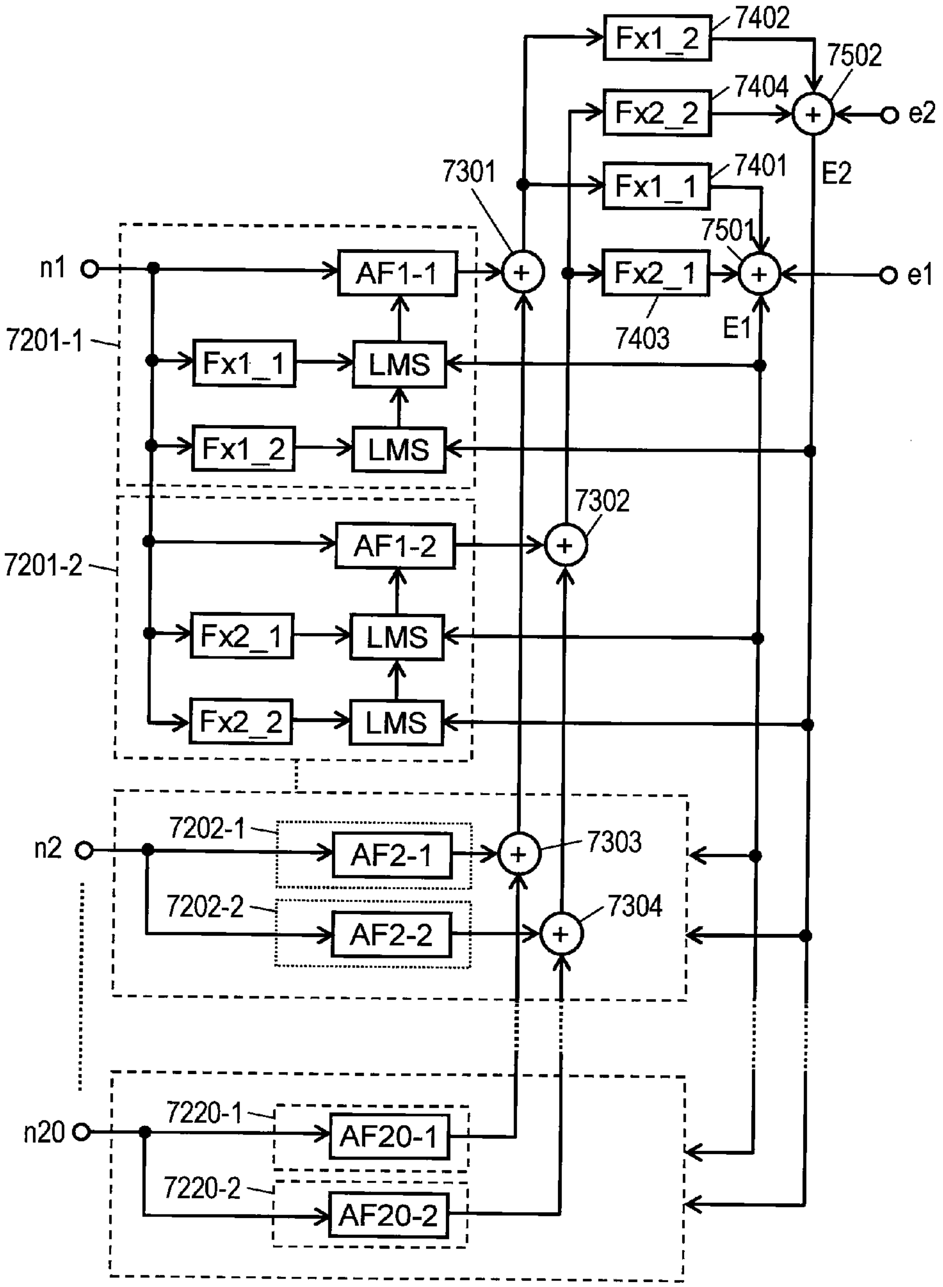
FIG. 12 shows a circuit diagram specifically depicting a filter coefficient calculator of the noise control device in accordance with the first embodiment of the present invention.

FIG. 12 shows a circuit structure of filter coefficient calculator 7000. In FIG. 12 only a structure that contributes to find filter coefficients of fixed filters 1201-1-1220-1 and 1201-2-1220-2 shown in FIG. 11 in order to simplify the description. As shown in FIG. 12 calculator 7000 includes adaptive filters 7201-1-7220-1, 7201-2-7220-2, adders 7301-7304, acoustic filters 7401-7404, and adders 7501-7502.

As shown in FIG. 11, noise signals n1-n20 from signal memory 7001 are supplied to adaptive filters 7201-1-7220-2. In adaptive filters 7201-1-7220-1, transfer function (Fx1_1) between control speaker 1401 and error microphone 7601 and transfer function (Fx1_2) between speaker 1401 and microphone 7602 have been set. These functions are necessary for the filtered-X_LMS method.

In a similar way, transfer function (Fx2_1) between speaker 1402 and microphone 7601 and transfer function (Fx2_2) between speaker 1402 and microphone 7602 have been set in adaptive filters 7201-2-7220-2 respectively.

Adaptive filters 7201-1-7220-1 have the noise signals processed by using the filter coefficients, and then supply the resultant signals as the control signals to adders 7301, 7303, and 7305, 7307, . . . , 7337 (not shown) respectively. Adder 7301 adds the control signals supplied from adaptive filters 7201-1-7220-1 together, and finally outputs the resultant signal to acoustic filters 7401 and 7402.

Adaptive filters 7201-2-7220-2 have the noise signals processed by using the filter coefficients, and then supply the resultant signals as the control signals to adders 7302, 7304, and 7306, 7308, . . . , 7338 (not shown) respectively. Adder 7302 adds the control signals supplied from adaptive filters 7201-2-7220-2 together, and finally outputs the resultant signal to acoustic filters 7403 and 7404.

Transfer coefficient (Fx1_1) between control speaker 1401 and error microphone 7601 has been set in acoustic filter 7401. Transfer coefficient (Fx1_2) between control speaker 1401 and error microphone 7602 has been set in acoustic filter 7402. Transfer coefficient (Fx2_1) between control speaker 14021 and error microphone 7601 has been set in acoustic filter 7403. Transfer coefficient (Fx2_2) between control speaker 1402 and error microphone 7602 has been set in acoustic filter 7404.

The signals having undergone acoustic filters 7401 and 7403 are supplied to adder 7501, which receives error signal "e1". Adder 7501 then adds these signals together. In a similar way, the signals having undergone acoustic filters 7402 and 7404 are supplied to adder 7502, which receives error signal "e2". Adder 7502 then adds these signals together.

Adaptive filters 7201-1-7220-2 regard the adding results by adders 7501-7502 as error signals E1-E2 which are used for renewing their own coefficients, and the adaptive filters renew their filter coefficients such that error signals E1-E2 can be minimized.

As shown in FIG. 11, noise signals n1-n20 and error signals e1-e4 are recorded as data for a given time, e.g. 1 (one) minute. Filter coefficient calculator 7000 thus can use the data repeatedly until filter coefficients of adaptive filters 7201-1-7220-2 converge on a certain value.

Filter coefficient calculator 7000 is independent of control filter 1000 that reproduces the control sounds from speakers 1401-1404, so that it can carry out its own job regardless of a process speed of filter 1000. In other words, filter 1000 does a real-time processing which should be done within a given sampling cycle, while calculator 7000 needs not finish its process within the real-time sampling cycle.

Noise signals n1-n20 and error signals e1-e4 have undergone the real-time sampling, so that even if the processes have taken more than the real time, the filter coefficients are calculated by calculator 7000 based on the sampling cycle.

In other words, the process times needed by calculator 7000 are independent of real time, so that if calculator 7000 has a structure which can complete a process within a shorter time, the structure will shorten a calculating time (converging time), i.e. working at a quicker speed than a sampling cycle allows finding a filter coefficient faster than a real time. On the other hand, if calculator 7000 has a structure which completes a process later than the real time, the structure will lower computation load, thereby reducing an amount of computation per unit time.

In the case of finishing the process later than the real time, it is not needed to complete all the processes shown in FIG. 12 within the sampling cycle. For instance, it is possible that some sample processes adaptive filter 7201-1 and the next sample processes adaptive filter 7201-2. (It is not necessarily to divide processes definitely for each one of structural elements as discussed above.)

The coefficient renewal processes discussed above allow filter coefficient calculator 7000 to calculate the filter coefficients that can reduce the noises arriving at the control points.

After the foregoing processes, when the filter coefficients renewed by adaptive filters 7201-1-7220-1 and 7201-2-7220-2 converge on a certain value, filter coefficient renewing section 5400 shown in FIG. 11 renews the filter coefficients set at fixed filters of control filter 1000 to the converged one at a given timing.

The given timing is, e.g. the timing at which the filter coefficients renewed by adaptive filters 7201-1-7220-1 and 7201-2-7220-2 have converged on the certain value, or the timing at which the filter coefficients of the fixed filters can be renewed once in several minutes, or once in several days. It can be the timing when the aircraft is put into service, or the in-flight equipment is updated.

Here is another structure: When the coefficients of adaptive filters 7201-1-7220-2 are renewed and converged on a certain value, filter coefficient renewing section 5400 gives an instruction to signal memory 7001 that it should record the noise signals and error signals at the converged time, and then filter coefficient renewing section 5400 provides the converged coefficients and the noise signals re-recorded with convolution computation in Af1_1, AF1_2, . . . , AF20_2 of adaptor filters 7201-1-7220-2. The resultant value of the convolution computation having undergone acoustic filters 7401-7404 are added to the error signals re-recorded together by adders 7501-7502. When the adding result falls within a given range, then filter coefficient renewing section 5400 can renew the filter coefficients of the fixed filters of control filter 1000 to calculated coefficients. This structure is also applicable to the present invention.

Even if filter coefficient calculator 7000 takes so long time for calculating the coefficients that a noise condition changes during that time, the structures discussed above can prevent speakers 1401-1404 from erroneously reproducing control sounds not appropriate to the actual situation. As a result, the structure discussed above can avoid giving unpleasant feeling to the passenger.

As discussed above the noise control device in accordance with the first embodiment allows filter coefficient calculator 7000 to calculate the optimum filter coefficients regardless of the real working time of control filter 1000, and also allows filter coefficient renewing section 5400 to renew the filter coefficients set to the fixed filters of control filter 1000 at a given timing. The foregoing mechanism allows calculating the filter coefficients optimum to the seat position and the ambient environment against a background where the noise control is actually done. On top of that, the request for a greater processing capacity of calculating the filter coefficients can be eased.

Since the filter coefficients calculated cannot be applied immediately to the fixed filters of control filter 1000, this mechanism can prevent the filter coefficients from being renewed to wrong filter coefficients. As a result, even if some inconvenience occurs, such as the coefficients disperse, it does not invite an actual reproduction of control sounds, so that the passenger can avoid being affected by unpleasant sounds.

The noise control device thus renews the filter coefficients set at the fixed filter of control filter 1000 to the coefficients optimum to the seat position and the ambient environment, thereby always providing the passenger with an optimum noise reduction effect.

Embodiment 2

Figure 13:
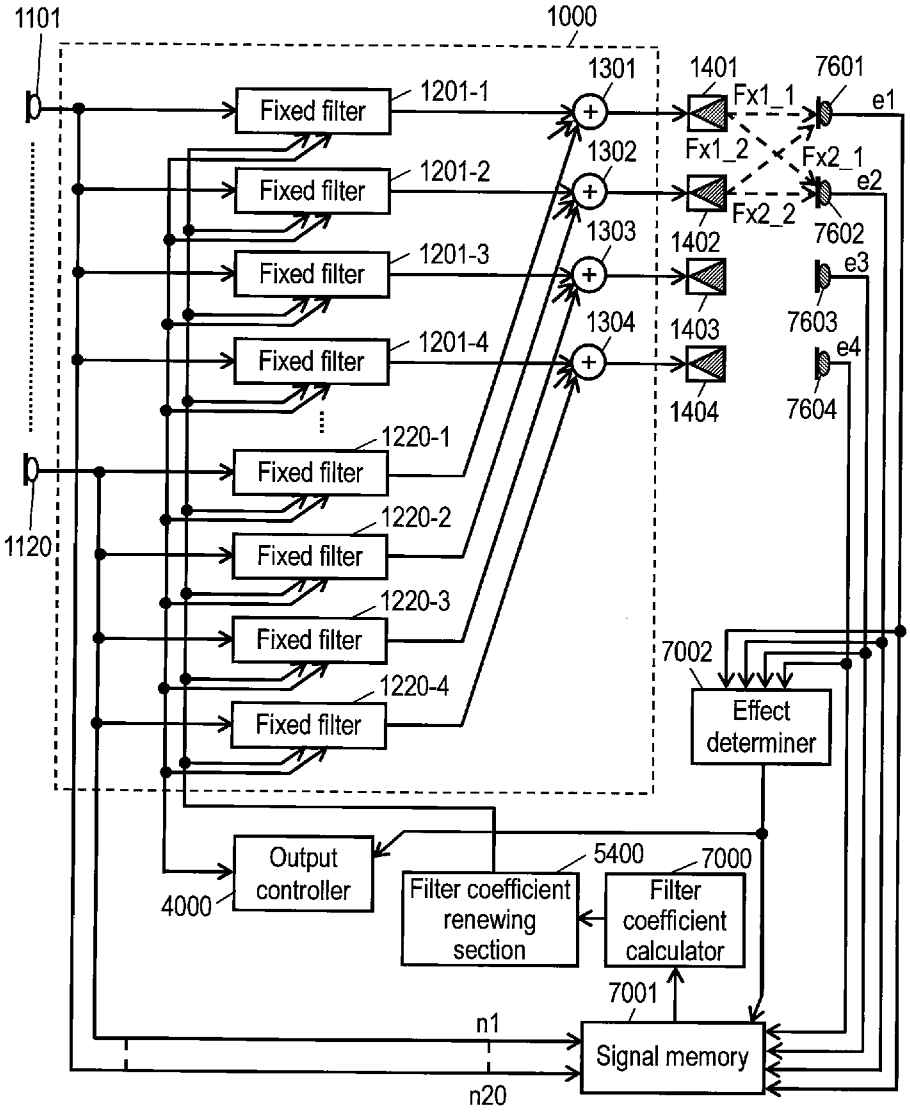
FIG. 13 shows a circuit diagram of a noise control device in accordance with a second embodiment of the present invention.

A structure of the noise control device in accordance with the second embodiment of the present invention is described hereinafter with reference to FIG. 13. As shown in FIG. 13, the noise control device comprises the following elements:

noise microphones 1101-1120;
control filter 1000;
control speakers 1401-1404;
output controller 4000;
filter coefficient renewing section 5400;
filter coefficient calculator 7000;
signal memory 7001;
effect determiner 7002; and
error microphones 7601-7604.

Effect determiner 7002 is newly added to the noise control device shown in FIG. 11, and the other elements remain unchanged and use the same reference signs.

First, the noise signals supplied from noise microphones 1101-1120 are processed with the fixed coefficients of fixed filters 1201-1-1220-4, and then reproduced by control speakers 1401-1404. This procedure is the same as that shown in FIG. 11.

In error microphones 7601-7604, the noises and the control sounds reproduced by control speakers 1401-1404 are synthesized, and the resultant signals are detected as error signals, which are then supplied to effect determiner 7002 for determining whether or not a predetermined noise reduction effect is achieved. The method of determining is, e.g. to extract a component within a noise control band from each one of the error signals, and then compare the level thereof before operating fixed filters 1201-1-1220-4 with the level thereof after the operation. Here are other instances: Average the levels of error signals before and after the operation within the control band, and then compare the levels with each other, or compare the levels at multiple representative frequencies within the control band.

When the determination results in a given effect, fixed filters 1201-1-1220-4 are kept operating for continuing the control. However, when the determination cannot find the given effect (including the case where noises increase although the effect does not degrade), it is notified to output controller 4000 that it is difficult to control the noises with the present control coefficients. Then controller 4000 halts the operation of fixed filters 1201-1-1220-4, and at the same time, effect determiner 7002 notifies signal memory 7001 of storing the signals.

Signal memory 7001 receives the notice, and then records noise signals n1-n20 supplied from noise microphones 1101-1120 and error signals e1-e4 supplied from error microphones 7601-7604 for a given time.

When the recording is ended, signal memory 7001 gives an instruction to filter coefficient calculator 7000 that it should start calculating the coefficients. Calculator 7000 then calculates the fixed filter coefficients of control filter 1000 by using the data recorded in signal memory 7001.

Filter coefficient renewing section 5400 reads the filter coefficients calculated by calculator 7000 at a given timing, and renews the filter coefficients set at the fixed filters of control filter 1000 to the filter coefficients read-out from calculator 7000. Filter coefficient calculator 7000 has the same structure as explained in the first embodiment shown FIG. 12.

As discussed above, the noise control device in accordance with the second embodiment determines the noise reduction effect of error microphones 7601-7604 by using the fixed filter coefficients of control filter 1000. If the effect does not fall within a given range, filter coefficient calculator 7000 calculates an optimum filter coefficient independently and regardless of the real-time work of control filter 1000. Filter coefficient renewing section 5400 renews, at a given timing, the filter coefficients set at the fixed filters of control filter 1000 to the filter coefficients calculated by calculator 7000.

The second embodiment thus renews the filter coefficients set in the fixed filters of control filter 1000 to the optimum ones in response to the seat position and the ambient environment, thereby achieving an optimum noise reduction effect at anytime. On top of that, the coefficient renewal discussed above can be done automatically, so that the time and labor needed for finding optimum coefficients to each one of the seats can be greatly reduced.

Embodiment 3

Figure 14:
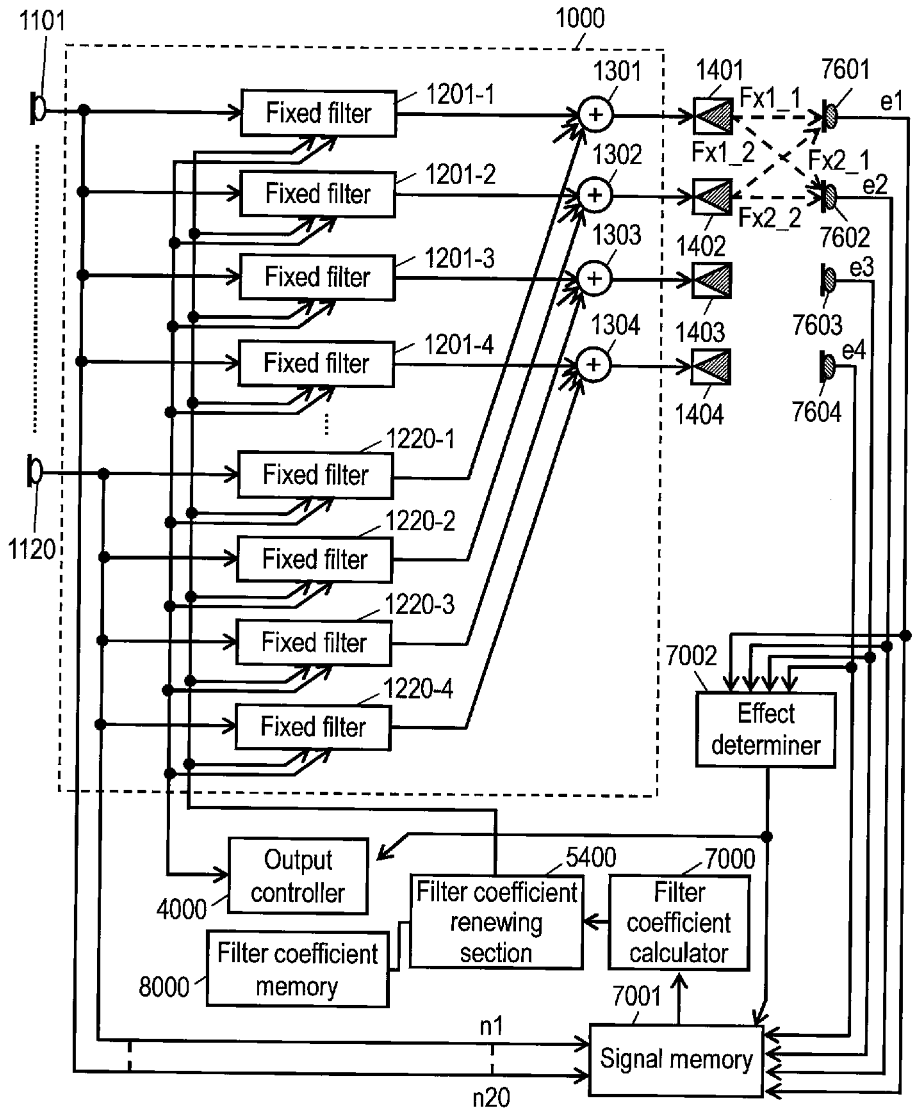
FIG. 14 shows a circuit diagram of a noise control device in accordance with a third embodiment of the present invention.
Figure 15:
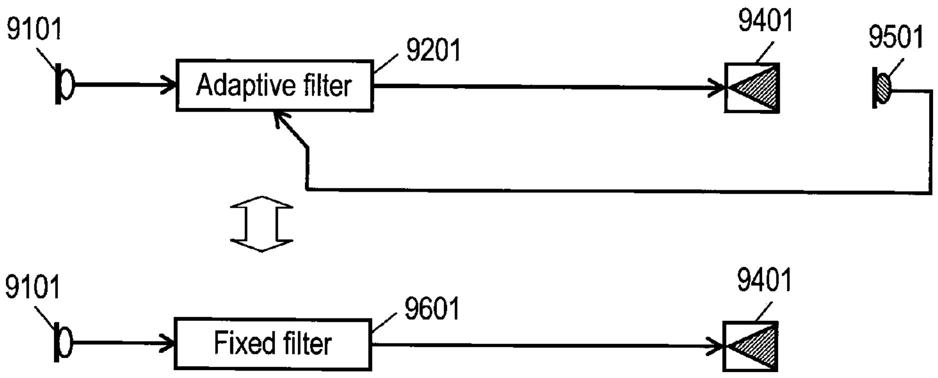
FIG. 15 PRIOR ART
FIG. 15 shows a circuit diagram of a conventional noise control device.

A structure of the noise control device in accordance with the third embodiment of the present invention is described hereinafter with reference to FIG. 14. As shown in FIG. 14, the noise control device comprises the following elements:

noise microphones 1101-1120;
control filter 1000;
control speakers 1401-1404;
output controller 4000;
filter coefficient renewing section 5400;
filter coefficient calculator 7000;
signal memory 7001;
effect determiner 7002;
error microphones 7601-7604; and
filter coefficient memory 8000.

Filter coefficient memory 8000 is newly added to the noise control device shown in FIG. 13, and the other elements remain unchanged and use the same reference signs. When the filter coefficients set at fixed filters 1201-1-1220-4 are renewed by filter coefficient renewing section 5400, filter coefficient memory 8000 stores the renewed coefficients.

The calculations done by calculator 7000 until the coefficients converge on some value largely depend on the initial values of filter coefficients set to the adaptive filters. When the aircraft cruises, the noises stay steady within a given range. The filter coefficients calculated previously seem to be rather close to the converging solution although the time has passed to a certain extent. Therefore use of the filter coefficients renewed previously and stored in filter coefficient memory 8000 as the initial values of the adaptive filters for the next calculation allows calculating the filter coefficients within a shorter time.

For instance, in a case where some service is provided to passengers, e.g. in an aircraft, if it takes a lot of time to calculate the filter coefficients, the passengers possibly feel unpleasant. It is thus important to calculate the filter coefficients within a shorter time.

If some structural elements other than filter coefficient memory 8000 become defective, and the noise control device should be replaced with new one, it is necessary to calculate the filter coefficients again. In this case, if filter coefficient memory 8000 has been built as a replaceable unit, it can take over the information about the filter coefficients previously renewed. This structure thus allows increasing the speed of re-calculating the filter coefficients in a case where the noise control device should be replaced with a new one due to malfunction.

In embodiments 1, 2, and 3, the adaptive filters in filter coefficient calculator 7000 and fixed filters 1201-1-1220-4 are described as totally different structural elements; however, the calculations can be common to both types of filters, so that both of the filters can be built in a common module. For instance, when the adaptive filters and the fixed filters are structured in a digital signal processor (DSP), use of the same source code and the same library allows building the noise control device in a more efficient manner.

What is claimed is:

1. A noise control device for reducing a given noise arriving at a control point by radiating a control sound toward the control point, the noise control device comprising:

a controlling noise detector for detecting the given noise and outputting a controlling noise signal;

a control filter for processing the controlling noise signal supplied from the controlling noise detector by using a fixed filter coefficient set in advance, and thereby outputting a control signal;

a control speaker radiating the control sound based on the control signal supplied from the control filter for reducing the given noise arriving at the control point;

an error detector placed at the control point for detecting an error signal between the given noise and the control sound that is supplied from the control speaker;

a signal memory for storing the controlling noise signal supplied from the controlling noise detector and the error signal detected by the error detector;

a filter coefficient calculator for calculating a filter coefficient by using the controlling noise signal and the error signal both stored in the signal memory;

a filter coefficient renewing section for renewing, at a given timing, the fixed filter coefficient set at the control filter to the filter coefficient calculated by the filter coefficient calculator; and an effect determiner for determining a signal level of the error signal detected by the error detector, wherein a start of said storing of the control noise signal and the error signal in the signal memory and a halt of operation of the control filter are controlled based on the signal level of the effect determiner.

2. The noise control device of claim 1, wherein the filter coefficient calculator includes:

an adaptive filter for signal-processing the controlling noise signal stored in the signal memory;

an acoustic filter for signal-processing an output from the adaptive filter; and an adder for adding an output signal from the acoustic filter to the error signal stored in the signal memory, wherein a transfer function from the control speaker to the error detector is set as a filter coefficient at the acoustic filter, and wherein the adaptive filter renews the filter coefficient such that an adding result supplied from the adder can be minimized as an error signal to be used for renewing a filter coefficient.

3. The noise control device of claim 2 further comprising:

a filter coefficient memory for storing a filter coefficient lastly renewed by the filter coefficient renewing section, wherein the adaptive filter uses a filter coefficient stored in the filter coefficient memory as an initial parameter.

4. The noise control device of claim 3, wherein the filter coefficient memory is a replaceable unit.

5. A noise control device for reducing a given noise arriving at a control point by radiating a control sound toward the control point, the noise control device comprising:

a controlling noise detector for detecting a given coming-noise and outputting a controlling noise signal;

a control filter for processing the controlling noise signal supplied from the controlling noise detector by using a fixed filter coefficient set in advance, and thereby outputting a control signal;

a control speaker radiating the control sound based on the control signal supplied from the control filter for reducing the given noise arriving at the control point;

an error detector placed at the control point for detecting an error signal between the given noise and the control sound that is supplied from the control speaker;

a signal memory for storing the controlling noise signal supplied from the controlling noise detector and an error signal detected by the error detector;

a filter coefficient calculator for calculating a filter coefficient by using the controlling noise signal and the error signal both stored in the signal memory;

a filter coefficient renewing section for renewing, at a given timing, a fixed filter coefficient set at the control filter to a filter coefficient calculated by the filter coefficient calculator;

an effect determiner for determining a signal level of the error signal detected by the error detector; and an output controller for receiving a result of determining by the effect determiner, wherein a start of the storing of the control noise signal and the error signal in the signal memory is controlled based on a determination result of the effect determiner;

wherein the output controller controls whether to keep or to halt an operation of the control filter, based on the result of determining by the effect determiner; and wherein the filter coefficient calculator calculates the filter coefficient regardless of a real working time of the control filter.

* * * * *